(12) United States Patent
Reis et al.

(10) Patent No.: US 8,901,352 B2
(45) Date of Patent: Dec. 2, 2014

(54) METHOD FOR THE SYNTHESIS OF RASAGILINE

(75) Inventors: Ömer Reis, Düzce (TR); Hasan Koyuncu, Düzce (TK); Ilker Esiringu, Düzce (TK); Yasemin Sahin, Düzce (TK); H. Ozan Gulcan, Düzce (TK)

(73) Assignee: Nobel Ilaç Sanayii Ve Ticaret A.S., Istanbul (TR)

( * ) Notice: Subject to any disclaimer, the term of this patent is extended or adjusted under 35 U.S.C. 154(b) by 0 days.

(21) Appl. No.: 13/979,028

(22) PCT Filed: Jan. 13, 2011

(86) PCT No.: PCT/TR2011/000004
§ 371 (c)(1),
(2), (4) Date: Sep. 25, 2013

(87) PCT Pub. No.: WO2012/096635
PCT Pub. Date: Jul. 19, 2012

(65) Prior Publication Data
US 2014/0018578 A1    Jan. 16, 2014

(51) Int. Cl.
*C07C 233/11*    (2006.01)
*C07C 209/62*    (2006.01)
*C07C 233/06*    (2006.01)

(52) U.S. Cl.
CPC ............. *C07C 209/62* (2013.01); *C07C 233/06* (2013.01); *C07B 2200/07* (2013.01); *C07C 2102/08* (2013.01); *C07C 233/11* (2013.01)
USPC .......................................... 564/211; 564/414

(58) Field of Classification Search
CPC ............................ C07C 233/11; C07C 209/62
USPC .................................................. 564/211, 414
See application file for complete search history.

(56) References Cited

U.S. PATENT DOCUMENTS

2005/0197365 A1    9/2005    Sterling et al.

FOREIGN PATENT DOCUMENTS

| CN | 101381314 A | 3/2009 |
| EP | 0436492 A2 | 7/1991 |
| EP | 2181980 A1 | 5/2010 |
| WO | WO-95/11016 A1 | 4/1995 |
| WO | WO-2009/147432 A1 | 12/2009 |
| WO | WO-2010/049379 A1 | 5/2010 |
| WO | WO-2011/087791 A1 | 7/2011 |

OTHER PUBLICATIONS

González-Díaz et al., "Mind-Best: Web server for drugs and target discovery; design, synthesis, and assay of MAO-B inhibitors and theoretical—experimental study of G3PDH protein from *Trichomonas gallinae*." J Proteome Res. 10:1698-718 (2011).
International Preliminary Report on Patentability for International Application No. PCT/TR2011/000004, issued Jul. 16, 2013 (4 pages).
International Search Report for International Application No. PCT/TR2011/000004, mailed Oct. 10, 2011 (4 pages).
Written Opinion for International Application No. PCT/TR2011/000004, mailed Oct. 10, 2011 (3 pages).

*Primary Examiner* — Shailendra Kumar
(74) *Attorney, Agent, or Firm* — Clark & Elbing LLP

(57) ABSTRACT

We have developed a new method for the synthesis of Rasagiline (Formula 1) based on the alkylation of trifluoroacetyl protected aminoindan. This protection enabled us to carry out an alkylation of aminoindan with a high yield and purity under very mild conditions with a wide range of reaction conditions and reagent selection. Considering the ease, purity and high yields of introducing and removal of the trifluoroacetyl group, this approach is a highly practical and economical way for the synthesis of rasagiline or its pharmaceutically acceptable salts.

17 Claims, No Drawings

METHOD FOR THE SYNTHESIS OF RASAGILINE

CROSS-REFERENCE TO RELATED APPLICATION

This application is the U.S. National Stage of International Application No. PCT/TR2011/000004, filed on Jan. 13, 2011, which is herein incorporated by reference.

Rasagiline and its synthesis were first reported in EP 0436492 B1. This reported synthesis was simply based on the alkylation of (R)-1-Aminoindan with propargyl chloride in acetonitrile in the presence of potassium carbonate at 60° C. for 16 hours. The crude product was highly impure and required further purification with column chromatography resulting in low overall yield (44%). This process has a long reaction time and the necessity for tedious chromatographic purification is not suitable for industrial applications.

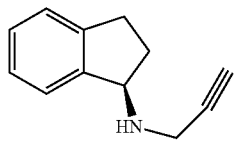

1

According to WO 95/11016, a similar alkylation strategy was reported in which propargyl benzenesulfonate was used instead of the corresponding chloride as the alkylating reagent. This reaction sequence was based on the use of racemic aminoindan and a subsequent resolution procedure. However, this approach also suffered from low yields and impure products.

In another application (WO 2009/147432), an improved alkylation procedure was offered in which reaction was carried out in THF at 0-5° C. and DBU was used as the advantageous base of choice. Although this reaction provides Formula 1 in 80-82% yield, it still affords a product with 64% purity (by HPLC).

Aforementioned processes for the synthesis of Rasagiline are based on the direct alkylation of aminoindan. Although alkylation is a straightforward and simple approach for the synthesis of primary or secondary amines, direct alkylation of amines are avoided strategically since this can lead to the formation of corresponding secondary or tertiary amines. Thus, if there is not any special chemical or physical attributes of the reactants or the product amine, direct alkylation will always result in a mixture over alkylated amine products, leading to low yields and purities.

One way to circumvent this problem is to protect the amine moiety as the corresponding amide and carry out the alkylation in a controlled manner. Amides are very weak nucleophiles and can only be alkylated by highly reactive special electrophiles. Although the alkylation of deprotonated amides under basic conditions is feasible, it is a rather difficult reaction because of their low nucleophilicity and high basicity. Moreover deprotonation of ordinary amides are usually carried out with strong bases (NaH, KH, amide bases, etc) in dry solvents.

In WO 20100493979, a similar alkylation strategy was reported. In this application, a carbamate protected aminoindan is alkylated in the presence of the strong base NaH in a dry solvent (DMF). The reaction product obtained was an oily residue and the overall yield following a chromatographic purification was %76-77. As mentioned above, this reaction has limitations (in terms of yield, purity, reaction conditions) due to the nature of the protecting group and the base employed.

Thus, there is still a need for an improved, practical, economical synthesis method that provides rasagiline in high yields and high purity simultaneously. Besides, this method should be amenable to scale up for industrial production.

In this respect we offered the trifluoroacetyl group as an amide protecting moiety for the synthesis of Rasagiline based on the following facts:

1. Trifluoroacetamides can be easily synthesized from cheap reactants with near quantitative yields,
2. Trifluoroacetamides are fairly acidic when compared to typical amides. Some representative examples are shown in Scheme 1. Hence, they can be easily deprotonated with mild bases in several solvents. Once they are deprotonated, corresponding anions will only be moderately basic that is necessary for a smooth high yield alkylation reaction. These attributes make their alkylation possible under mild conditions where other typical amides or carbamates would be unreactive or react sluggishly.

Scheme 1.

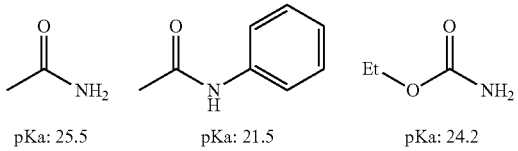

pKa: 25.5    pKa: 21.5    pKa: 24.2

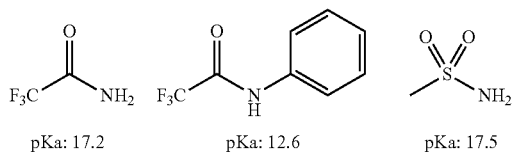

pKa: 17.2    pKa: 12.6    pKa: 17.5

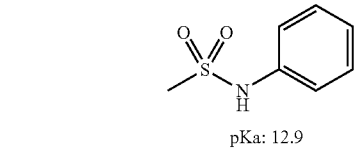

pKa: 12.9

3. Trifluoroacetamides can be hydrolyzed very easily under mild reaction conditions with high yields.

These properties of trifluoroacetamides make them superior to the other potentially useful amide derivatives such as sulfonamides (Scheme 1). Although sulfonamides are good candidates for such an alkylation strategy, their removal are problematic and requires harsh reaction conditions or special reactants.

Synthesis of Rasagilin, based on our proposed amide alkylation strategy, starts with the reaction of (R)-1-Aminoindan (Formula 2) with trifluoroacetic anhydride in the presence of pyridine (Scheme 2). This reaction affords pure protected amide Formula 3 in 95% yield. This reaction step is highly flexible and can be carried out with various trifluoroacetyl donating groups, bases and solvents (Greene, T. W.; Protective Groups in Organic Synthesis, p. 556).

Scheme 2.

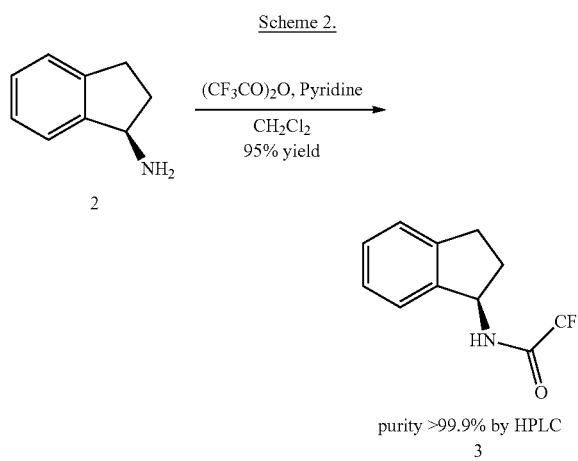

purity >99.9% by HPLC
3

Alkylation of Formula 3 was tested with different bases in several solvents. First, it was found out that this reaction is effective with various bases. For example; NaOtBu or KOtBu was convenient for this reaction and corresponding alkylated amide could be obtained with quantitative conversion. These bases provided a fast and irreversible deprotonation of Formula 3 at RT. Reaction of the resulting amide anion with Propargyl bromide (or similar propargyl electrophiles) furnished the desired product in very short reaction times.

Among the milder carbonate bases, $Cs_2CO_3$ (1-1.2 eq.) was found to be very effective. It provided the product with full conversion of the starting material under mild reaction conditions with excellent purity (>97.5% purity). Although the reaction with $K_2CO_3$ was sluggish, we found that this reaction could be run efficiently with $K_2CO_3$, when catalytic amount of $Cs_2CO_3$ (0.1-0.5 eq. $Cs_2CO_3$, 2-5 eq. $K_2CO_3$) was employed. We consider that the solubility of the $Cs_2CO_3$ in organic solvents is very important for its superiority over $K_2CO_3$. The coordinating abilities of the soft Cesium center should also be taken in to account. This reaction can be run without any solvent or in various solvents like DMF, acetonitrile, THF, DCM, toluene etc. However, reaction times were noticeably shorter in DMF or acetonitrile under identical reaction conditions (0.1-8 h depending on the reaction conditions employed).

Alkylation can be performed with or without the phase transfer catalyst (PTC) Tetrabutylammonium iodide (TBAI), but beneficial effects for its use are observed for certain combinations of solvents and bases. This observation is in contrast with the most amide alkylation reactions employing carbonate bases where a high load of PTC is generally necessary for an efficient reaction. Although similar conversion rates were observed in $Cs_2CO_3$ promoted alkylations with or without TBAI, its use had a detrimental effect on the reaction rate in NaOtBu promoted alkylations. This can be explained on the basis that complete and irreversible deprotonation occurs with Nat-BuO and the alkylation is rate determining step in which reaction takes place via the more reactive reagent propargyl iodide in the presence of TBAI. On the contrary, deprotonation of amide is the critical step in the $Cs_2CO_3$ promoted alkylations.

This reaction can be run with several propargyl donating alkylating reagents with an appropriate leaving group (X, Y). Besides, different alkylating reagents that are subsequently transformed into an alkyne can also be utilized, such as alkylating reagents allyl bromide or chloroallyl chloride derivates (Formula 7 or Formula 8) etc.

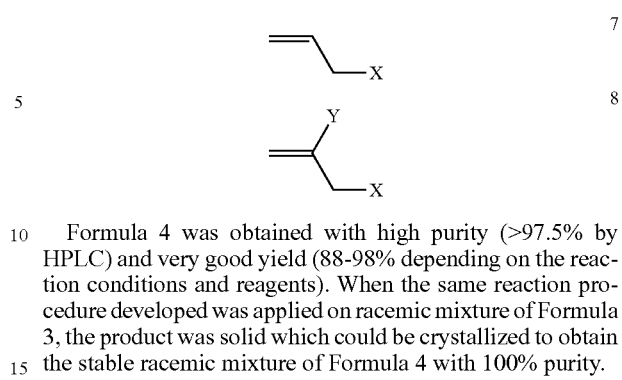

Formula 4 was obtained with high purity (>97.5% by HPLC) and very good yield (88-98% depending on the reaction conditions and reagents). When the same reaction procedure developed was applied on racemic mixture of Formula 3, the product was solid which could be crystallized to obtain the stable racemic mixture of Formula 4 with 100% purity.

Scheme 3.

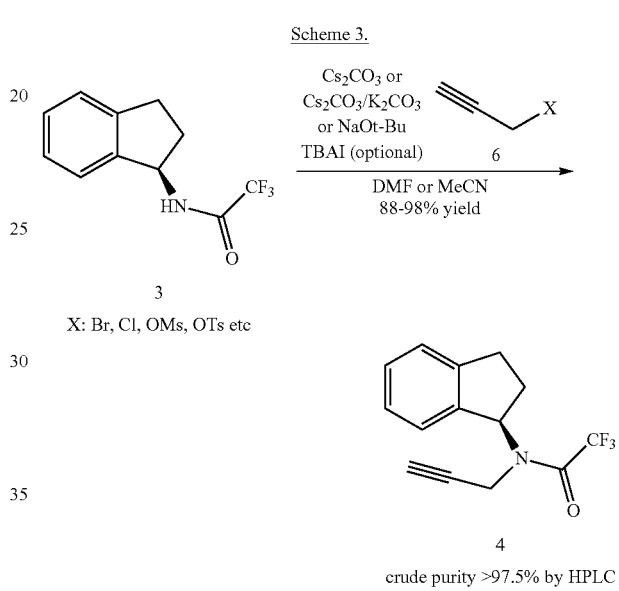

X: Br, Cl, OMs, OTs etc crude purity >97.5% by HPLC

Removal of a trifluoroacetyl protecting group from an amine functionality can be accomplished under many different reaction conditions (Greene, T. W.; Protective Groups in Organic Synthesis, p. 557). In our process, hydrolysis of Formula 4 was carried out at room temperature in basic aqueous methanol solution providing the rasagiline base quantitatively with excellent purity (>99.5% by HPLC). Reaction could also be run in MeCN with a similar efficiency. The choice of solvent is not limited to MeOH or MeCN, both water miscible and immiscible solvents can be used as the reaction medium. Reaction could also be run without any solvent. Briefly, trifluoroacetyl group was easily hydrolyzed under this mild condition and provided the corresponding rasagiline in high purity and yield in a quick reaction (15-30 min at RT, Scheme 4).

Scheme 4.

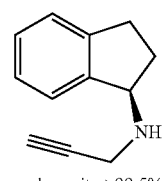

crude purity >99.5%

1

Formula 1 could easily be transformed in to the corresponding Rasagiline mesylate (Formula 5) according to previously published methods. When a three step reaction sequence (alkylation, hydrolysis and mesylate salt formation) starting from Formula 3 was run, Formula 5 was obtained in 88% overall yield with 100% purity (Scheme 5). None of the intermediates of this reaction sequence was subjected to purification except for simple extraction and filtration operations. Preferably, the above mentioned process can be carried our in one pot.

Scheme 5.

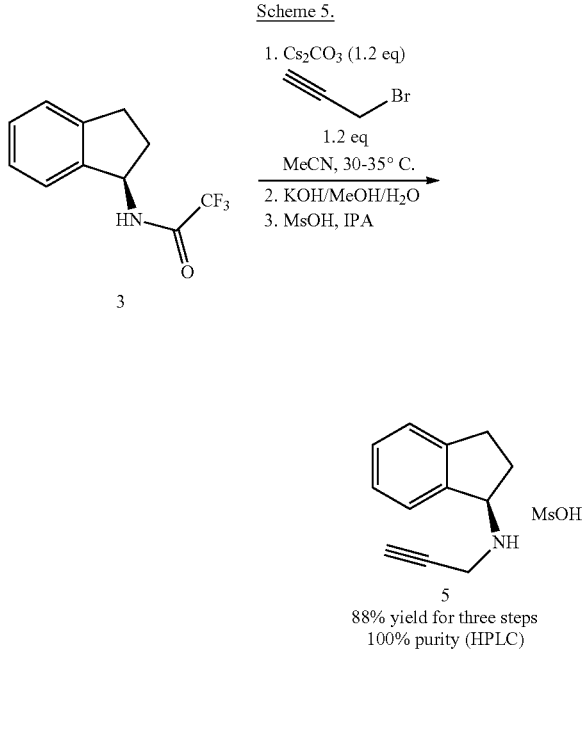

88% yield for three steps
100% purity (HPLC)

EXAMPLES

Preparation of Trifluoroacetyl Protected Aminoindan 3:

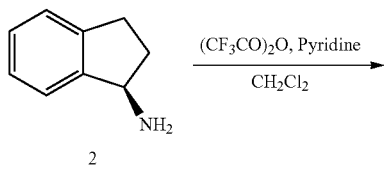

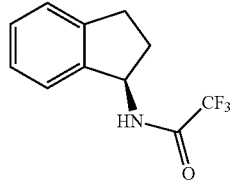

3

(R)-Aminoindan HCl salt (50 g, 0.29 mol) was placed in a round bottom flask followed by DCM (196 mL) and pyridine (55.8 g, 0.7 mol, 2.4 eq.). Flask was placed in an ice bath and TFAA (74.3 g, 0.35 mol, 1.2 eq.) was added dropwise onto the resulting solution in 15-20 min. Reaction mixture was stirred for 15 min at room temperature. After the end of 15 min, a TLC sample indicated the complete consumption of the starting material and reaction mixture was washed with 2×1 N HCl, 2×1 N NaOH solution and brine solution. Collected organic phases, dried upon $MgSO_4$, were filtered, evaporated to dryness and the residue left was dried in an oven at 40-50° C. to obtain 64.2 g off-white solid in 95% yield (purity >99.5% by HPLC).

$^1$H-NMR ($CDCl_3$): δ 7.14-7.26 (4H, m); 6.43 (1H, bs); 5.42 (1H, dd, J=15 Hz, 7.7 Hz); 2.78-3.05 (2H, m); 2.52-2.65 (1H, m); 1.78-1.92 (1H, m)

Preparation of Rasagiline Mesylate 5:

1. Alkylation of Formula 3

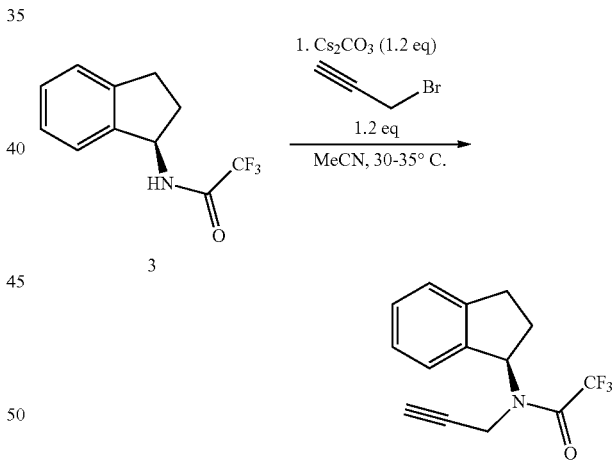

$Cs_2CO_3$ (34.2 g, 104.8 mmol, 1.2 eq.), Formula 3 (20 g, 87.3 mmol) and 85 mL MeCN was placed in a round bottom flask and stirred at 30-35° C. for 10 min. After the end of 10 min, propargyl bromide (15.6 g 80% toluene solution, 12.5 g, 1.2 eq.) was added via syringe and the resulting mixture was stirred at 30-35° C. until HPLC analysis showed complete conversion (4 h, 99.9% conversion, purity >99% according to analysis of the reaction mixture) of the starting material. After the completion of the reaction, mixture was filtered to obtain a clean yellowish solution that was evaporated to dryness furnishing Formula 4 (97.8% purity bu HPLC) as a mixture of two geometrical isomers in a ~1:3.5 ratio.

Major Isomer:
¹H-NMR (CDCl₃): δ 7.05-7.28 (4H, m); 5.50-5.62 (1H, m); 4.07 (1H, dd, J=2.4 Hz, 18 Hz); 3.45 (1H, dd, J=17.3 Hz, 2.6 Hz); 3.0-3.2 (1H, m); 2.8-2.95 (1H, m); 2.25-2.55 (1H, m); 2.11 (1H, t, J=2.4 Hz)

Minor Isomer:
¹H-NMR (CDCl₃): δ 7.05-7.28 (4H, m); 5.96-6.05 (1H, m); 4.09 (1H, dd, J=2.4 Hz, 19 Hz); 3.60-3.71 (1H, m); 3.0-3.2 (1H, m); 2.8-2.95 (1H, m); 2.25-2.55 (2H, m); 2.18 (1H, t, J=2.4 Hz)

2. Hydrolysis

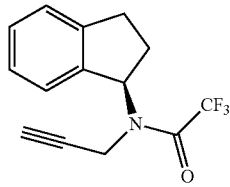

4

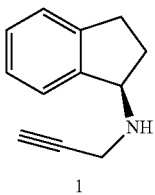

1

Yellowish-red oil from step 1 was dissolved in MeOH (140 mL) and 20% KOH solution (58 mL) was added to obtain a homogeneous solution. Reaction mixture was stirred at 30-35° C. until completion of the starting material as indicated by TLC and HPLC. After the completion of the reaction (>99.9 conversion after 30 min, purity >99.5%), MeOH was evaporated and the aqueous phase was extracted with MTBE. Combined organic phases were dried over MgSO₄ and filtered to obtain a bright yellow solution which was evaporated to dryness in a rotary evaporator, afforded Formula 1 as an oil (14.3 g, >99.5 HPLC purity).

3. Salt Formation

Crude rasagiline base from the hydrolysis step was dissolved in i-PrOH (75 mL), filtered and heated to 50-60° C. MsOH (8.04 g, 83.6 mmol, 1.0 eq.) was added dropwise in 5-10 min, seeded with Rasagiline mesylate crystal resulting in a fast crystallization of the product. Solution was further stirred for 15 min at this temperature after which the solution was cooled down to room temperature, filtered and washed with cold IPA to obtain 20.5 g Rasagiline mesylate as white crystals in 88% overall yield starting from Formula 3 and 100% purity (by HPLC).

The invention claimed is:

1. A compound of Formula 4 or a salt thereof,

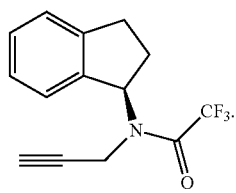

4

2. A process for the preparation of a compound of Formula 1 or a salt thereof, said process comprising the steps of;

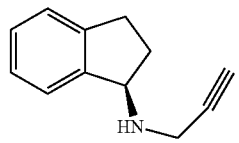

1

(a) alkylating a protected amide compound of Formula 3

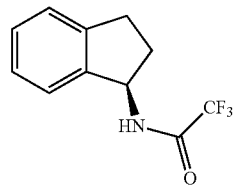

3 with a compound of Formula 6 or an alkylating reagent that can be transformed into an alkyne,

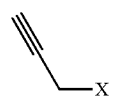

6 in the presence of a base to obtain a compound of Formula 4

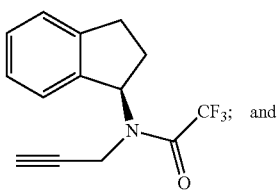

4

(b) hydrolyzing the compound of Formula 4 to obtain the compound of Formula 1 or a salt thereof.

3. The process according to the claim 2, wherein the protected amide compound of Formula 3 is obtained by reacting a compound of Formula 2 with a trifluoroacetyl donating group

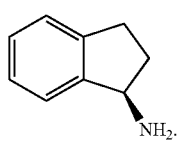

2

4. The process according to claim 2, wherein the alkylating reagent used in the reaction is a compound of Formula 6.

5. The process according to claim 2, wherein step (a) is carried out in the presence of a base selected from the group consisting of NaOtBu, KOtBu, Cs₂CO₃, and a mixture of Cs₂CO₃ and K₂CO₃.

6. The process according to claim 2, wherein step (a) is carried out in the presence of a phase transfer catalyst.

7. The process according to claim 6, wherein the phase transfer catalyst is TBAI.

8. The process according to claim 2, wherein step (a) is carried out in a solvent.

9. The process according to claim 8, wherein the solvent is DMF or acetonitrile.

10. The process according to claim 2, wherein step (b) is carried out in a solvent.

11. The process according to claim 2, wherein step (b) is carried out with a base.

12. The process according to claim 2, wherein the salt is a mesylate salt of Formula 1.

13. The process according to claim 2, wherein said process is carried out in one pot.

14. The process according to claim 3, wherein said process is carried out in one pot.

15. The process according to claim 2, wherein said alkylating reagent that can be transformed into an alkyne is a compound of Formula 7 or Formula 8

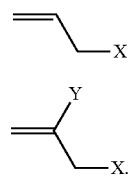

16. The process according to claim 2, further comprising step (c) converting the compound of the Formula 1 to its salt.

17. The compound of claim 1 wherein said compound is in a racemic mixture.

* * * * *

UNITED STATES PATENT AND TRADEMARK OFFICE
CERTIFICATE OF CORRECTION

PATENT NO. : 8,901,352 B2  
APPLICATION NO. : 13/979028  
DATED : December 2, 2014  
INVENTOR(S) : Ömer Reis et al.

Page 1 of 1

It is certified that error appears in the above-identified patent and that said Letters Patent is hereby corrected as shown below:

Title page item (75), under Inventors, replace "Hasan Koyuncu, Düzce (TK)" with --Hasan Koyuncu, Düzce (TR)--;

replace "Ilker Esiringu, Düzce (TK)" with --Ilker Esiringu, Düzce (TR)--;

replace "Yasemin Sahin, Düzce (TK)" with --Yasemin Sahin, Düzce (TR)--;

replace "H. Ozan Gulcan, Düzce (TK)" with --H. Ozan Gulcan, Düzce (TR)--.

Signed and Sealed this  
Fourth Day of August, 2015

Michelle K. Lee  
*Director of the United States Patent and Trademark Office*